US007696361B2

(12) United States Patent
Beauchamp et al.

(10) Patent No.: US 7,696,361 B2
(45) Date of Patent: Apr. 13, 2010

(54) CHEMICAL REAGENTS CAPABLE OF SELECTIVE ATTACHMENT TO AND REACTION WITH PEPTIDES AND PROTEINS

(75) Inventors: Jesse L. Beauchamp, La Canada, CA (US); Ryan R. Julian, Bloomington, IN (US); Brian M. Stoltz, Pasadena, CA (US); Jeremy A. May, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1060 days.

(21) Appl. No.: 10/782,373

(22) Filed: Feb. 18, 2004

(65) Prior Publication Data
US 2005/0010059 A1 Jan. 13, 2005

Related U.S. Application Data

(60) Provisional application No. 60/448,290, filed on Feb. 19, 2003.

(51) Int. Cl.
*C07D 321/00* (2006.01)
(52) U.S. Cl. ........................ 549/347; 549/346
(58) Field of Classification Search ................. 549/347, 549/346
See application file for complete search history.

(56) References Cited

OTHER PUBLICATIONS

Fredrick et al., Chem. abs. vol. 94 No. 134248, J. Chem. Soc. Chem. Comm. v.24 pp. 1211-12 (1980) abstract, best avaiible.*
Dugas et al, Chem. Abs. vol. 115 No. 71563, Syn. v.5 pp. 420-2 (1991) abstract, best avaiible.*
Mascagni et al, J. Chem. Soc. Perkin Trans. II (1987) pp. 323-327.*
Bell et al. (1999), "A Small-Molecule Guanidinium Receptor: The Arginine Cork," *Angew. Chem. Int. Ed.* 38(17):2543-2547.
Bradshaw et al. (1996), "Crown Ethers," *Comprehensive Supramolecular Chemistry* 1:35-95, G.W. Gokel (Ed.) Pergamon/Elsevier, Oxford.
Chandler et al. (1981), "Synthesis of Some 2,9-Disubstituted-1, 10-Phenanthrolines," *J. Heterocycl. Chem.* 18:599-601.
Friess et al. (2001), "Protein Structure Information from Mass Spectrometry? Selective Titration of Arginine Residues by Sulfonates," *J. Am. Soc. Mass Spectrom.* 12:810-818.
Galan et al. (1992), "A Receptor for the Enantioselective Recognition of Phenylalanine and Tryptophan Under Neutral Conditions," *J. Am. Chem. Soc.* 114:1511-1512.
Hu et al. (1995), "Gas-Phase Coordination Properties of $Zn^{2+}$, $Cu^{2+}$, $Ni^{2+}$, and $Co^{2+}$ with Histidine-Containing Peptides," *J. Am. Chem. Soc.* 117(45):11314-11319.
Julian et al. (2001), "Site Specific Sequestering and Stabilization of Charge in Peptides by Supramolecular Adduct Formation with 18-Crown-6 Ether by Way of Electrospray Ionization," *Int. J. Mass Spectrom.* 210/211:613-623.
Julian et al. (2002), "Molecular Recognition of Arginine in Small Peptides by Supramolecular Complexation with Dibenzo-30-crown-10 Ether," *Int. J. Mass Spectrom.* 220:87-96.

Julian et al. (2002), "The Unusually High Proton Affinity of Aza-18-crown-6 Ether: Implications for the Molecular Recognition of Lysine in Peptides by Lariat Crown Ethers," *J. Am. Soc. Mass Spectrom.* 13:493-498.
Julian et al. (2003), "Molecular Mousetraps: Gas-Phase Studies of the Covalent Coupling of Noncovalent Complexes Initiated by Reactive Carbenes Formed by Controlled Activiation of Diazo Precursors," *Angew. Chem. Int. Ed.* 42(9):1012-1015.
Lee et al. (1998), "Salt Bridge Chemistry Applied to Gas-Phase Peptide Sequencing: Selective Fragmentation of Sodiated Gas-Phase Peptide Ions Adjacent to Aspartic Acid Residues," *J. Am. Chem. Soc.* 120(13):3188-3195.
Lee et al. (1998), "Selective Binding of Crown Ethers to Protonated Peptides Can Be Used to Probe Mechanisms of H/D Exchange and Collision-Induced Dissociation Reactions in the Gas Phase," *J. Am. Chem. Soc.* 120(23):5800-5805.
Lin et al. (1998), ."C-Terminal Peptide Sequencing via Multistage Mass Spectrometry," *Anal. Chem.* 70(24):5162-5165.
Ludwig (2000), "Calixarenes in Analytical and Separation Chemistry," *Fresenius J. Anal. Chem.* 367:103-128.
Maleknia et al. (1993), "Cavity-Size-Dependent Dissociation of Crown Ether/Ammonium Ion Complexes in the Gas Phase," *J. Am. Chem. Soc.* 115(7):2837-2843.
Nemirovskiy et al. (1998), "Gas Phase Studies of the Interactions of $Fe^{2+}$ with Cysteine-Containing Peptides," *J. Am. Soc. Mass Spectrom.* 9:1285-1292.
Ngola et al. (1999), "A Selective Receptor for Arginine Derivatives in Aqueous Media. Energetic Consequences of Salt Bridges That Are Highly Exposed to Water," *J. Am. Chem. Soc.* 121(6):1192-1201.
Rensing et al. (2001), "Optimization of a Synthetic Arginine Receptor. Systematic Tuning of Noncovalent Interactions," *J. Org. Chem.* 66(17):5814-5821.
Schrader (1998), "Strong Binding of Arylguanidinium Ions by Benzylic Bisphosphonates—Evidence for π-cation and π,π-interactions," *Tetrahedron Letters* 39:517-520.
Steen et al. (2002), "Analysis of Protein-Nucleic Acid Interactions by Photochemical Cross-Linking and Mass Spectrometry," *Mass Spectrom. Rev.* 21:163-182.
Tsaprailis et al. (1999), "Influence of Secondary Structure on the Fragmentation of Protonated Peptides," *J. Am. Chem. Soc.* 121(22):5142-5154.
Tsaprailis et al. (2000), "Refining the Model for Selective Cleavage at Acidic Residues in Arginine-Containing Protonated Peptides," *Int. J. Mass Spectrom.* 195/196:467-479.
Weijnen et al. (1992), "Functionalised 1,10-Phenanthroline Metal-locatalysts as Models for Hydrolytic Metalloenzymes," *J. Chem. Soc. Perkin Trans.* 2:829-834.
Julian et al. (2004), *J. Am. Soc. Mass Spectrom.*, 15:616-624.
Keough et al. (2003), *Analytical Chem.*, 75(7):156A-165A.

* cited by examiner

*Primary Examiner*—Janet L. Andres
*Assistant Examiner*—Raymond Covington
(74) *Attorney, Agent, or Firm*—Isaac M. Rutenberg; Mintz Levin Cohn Ferris Glovsky and Popeo PC

(57) ABSTRACT

Biomimetic reagents capable of selectively forming non-covalent complexes and initiating intermolecular reactions with peptides in the gas phase are described. The reagents are particularly useful in gas phase peptides chemistry.

27 Claims, No Drawings

CHEMICAL REAGENTS CAPABLE OF SELECTIVE ATTACHMENT TO AND REACTION WITH PEPTIDES AND PROTEINS

CROSS REFERENCE TO RELATED APPLICATIONS

This application claims priority under 35 U.S.C. §119(e)(1) to U.S. Provisional Application Ser. No. 60/448,290 filed Feb. 19, 2003.

ACKNOWLEDGEMENT OF GOVERNMENT SUPPORT

This invention was made with Government Support under NSF Grant No. CHE-9727566. The Government has certain rights to this invention.

FIELD OF THE INVENTION

This invention relates to reagents useful in the synthesis of amine-containing compounds, and particularly gas phase peptide chemistry. The invention also relates to the use of diazo-based reagents that bind to and become covalently attached to amino acid residues, particularly residues containing primary amines. The invention further relates to the use of reagents containing acidic groups or transition metal binding functionalities that initiate selective cleavage of amino acid residues, particularly residues containing primary amines.

BACKGROUND OF THE INVENTION

Molecular recognition is a powerful technique that can be used to generate noncovalently bound host-guest complexes for a variety of purposes. These noncovalent complexes are easily transferred to the gas phase by electrospray ionization (ESI). Unfortunately, attempts to effect intermolecular reactions between the cluster components are often frustrated by the lability of noncovalent complexes, which results from the relatively weak interactions that hold them together.

In the post genomic world of proteomics, many substantial advances will be made through experiments conducted in the gas phase. Therefore, the understanding and control of gas phase peptide chemistry is of paramount importance. For example, the study of gas phase peptide chemistry has revealed that selective cleavage of the peptide backbone will occur at aspartic acid residues (Tsaprailis et al (2000) *Int. J. Mass Spectrom.* 195/196:467; Tsaprailis et al. (1999) J. Am. Chem. Soc. 121:5142; Lee et al. (1998) *J. Am. Chem. Soc.* 120:3188). This cleavage occurs by a displacement reaction that yields a stable five-membered ring. Understanding this phenomenon allows for the accurate prediction of peptide cleavages in aspartic acid containing peptides. Furthermore, C-terminal peptide sequencing via a similar mechanism, where the C-terminal amino acids are sequentially removed, has also yielded promising, if limited, results (Lin et al. (1998) *Anal. Chem.* 70:5162). Unfortunately, this C-terminal sequencing is limited to peptides with eight amino acids or less, severely limiting the utility of this technique for sequencing proteins in the gas phase. The addition of transition metals can also mediate peptide chemistry in the gas phase (Hu et al. (1995) *J. Am. Chem. Soc.* 117:11314; Nemirovskiy et al. (1998) *J. Am. Soc. Mass Spectrom.* 9:1285). Preliminary studies have shown that $Zn^{2+}$, $Ni^{2+}$, and $Co^{2+}$ will attach to histidine and promote peptide fragmentation at this residue (Hu et al. (1995) *J. Am. Chem. Soc.* 117: 11314). These experiments were carried out on a very limited sampling of peptides, but the resulting cleavages were highly specific. Similarly, $Fe^{2+}$ complexes with cysteine containing peptides enhanced the number of cleavages observed at the cysteine residues when the peptide was collisionally activated. These important initial results illustrate that peptide chemistry can be influenced by the addition of appropriate reagents.

A significant amount of work developing reagents that selectively recognize and non-covalently attach to specific amino acid side chains has already been reported (Julian et al. (2001) *Int. J. Mass. Spectrom.* 210:613-623). Reagents have been developed specificity for the gas phase, as described in Friess et al. (2001) *J. Am. Soc. Mass Spectrom.* 12(7):810 and Julian et al. (2002) *Int. J. Mass Spectrom.* 220:87. Solution phase reagents are described in Bell et al. (1999) *Angew. Chem. Int. Ed.* 38:2543; Galan et al. (1992) *J. Am. Chem. Soc.* 114:1511; Ludwig et al. (2000) *Anal. Chem.* 367:103; Ngola et al. (1999) *J. Am. Chem. Soc.* 121:1192; Rensing et al. (2001) *J. Org. Chem.* 66:5814; and Schrader (1998) *Tetrahedron Lett.* 39:517).

The instant invention addresses the needs in the art by the use of reagents that are based upon crown ethers. Crown ethers, and 18-crown-6 ether (18C6) in particular, are well known hosts for protonated primary amines, both in solution and in the gas. More recently, 18C6 was shown to selectively bind to lysine residues in small peptides (Julian et al. (2001) *Int. J. Mass Spectrom.* 210:613-623).

SUMMARY OF THE INVENTION

One aspect of the invention relates to reagents that are capable of selectively forming non-covalent complexes and initiating intermolecular reactions with amine-containing compounds, particularly in the gas phase, comprising at least one crown ether group and a moiety selected from acidic groups, transition metal binding groups and diazo groups.

Another aspect of the invention relates to a method of selectively forming non-covalent complexes and initiating intermolecular reactions with amine-containing compounds, comprising reacting the amine-containing compound with a second compound comprising at least one crown ether group and a moiety selected from acidic groups, transition metal binding groups and diazo groups.

Yet another aspect of the invention pertains to a method of initiating peptide backbone cleavage comprising adding a compound to the peptide, where the added compound comprises at least one crown ether group and a moiety selected from acidic groups and transition metal binding groups.

Still another aspect of the invention relates to a method of covalently attaching to an amino acid via carbene insertion chemistry comprising adding a compound to an amino acid-containing compound, where the added compound comprises at least one crown ether group and a diazo group.

DETAILED DESCRIPTION OF THE INVENTION

In describing detailed embodiments of the invention, certain definitions are set forth that are used in describing the invention. These definitions apply only to the terms as they are used in this patent and may not be applicable to the same terms as used elsewhere, for example in scientific literature or other patents or applications including other applications by these inventors or assigned to common owners. The following description of the preferred embodiments and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature.

It must be noted that, as used in this specification and the appended claims, the singular forms "a", "an" and "the" include plural referents unless the context clearly dictates otherwise. Thus, for example, reference to "a reagent" includes a mixture of two or more such reagents, reference to "an amino acid residue" includes two or more such residues, and the like.

The term "alkyl" as used herein refers to a linear, branched or cyclic saturated hydrocarbon group typically although not necessarily containing 1 to about 20 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain about 1-12 carbon atoms. The term "lower alkyl" intends an alkyl group of 1-6 carbon atoms, and the specific term "cycloalkyl" intends a cyclic alkyl group, typically having 4-8, preferably 5-7, carbon atoms. The term "alkyl" is also intended to include alkyl groups substituted with one or more substituent groups. The term "heteroalkyl" refers to an alkyl group in which at least one carbon atom is replaced with a heteroatom.

The term "alkenyl" as used herein refers to a linear, branched or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like, as well as cycloalkenyl groups. Preferred alkenyl groups herein contain 2-12 carbon atoms. The term "lower alkenyl" intends an alkenyl group of 2-6 carbon atoms, and the specific term "cycloalkenyl" intends a cyclic alkenyl group, preferably having 5-8 carbon atoms. The term "alkenyl" is also intended to include alkenyl groups substituted with one or more substituent groups. The term "heteroalkenyl" refers to an alkenyl group in which at least one carbon atom is replaced with a heteroatom.

The term "aryl" as used herein refers to an aromatic substituent containing a single aromatic ring or multiple aromatic rings that are fused together, directly linked, or indirectly linked (such that the different aromatic rings are bound to a common group such as a methylene or ethylene moiety), generally containing in the range of 5 to about 24 carbon atoms. Preferred aryl groups contain one aromatic ring or 2-4 fused or linked aromatic rings, e.g., phenyl, naphthyl, biphenyl, and the like. The term "aryl" is also intended to include aryl groups substituted with one or more substituent groups. The term "heteroaryl" refers to an aryl group in which at least one carbon atom is replaced with a heteroatom.

The term "alkaryl" refers to an aryl group that has an alkyl substituent, and the term "alkheteroaryl" refers to a heteroaryl group with an alkyl substituent.

The present invention relates to biomimetic reagents useful in the selective forming of non-covalent (e.g., hydrogen bonding, electrostatics, van der Waals forces, hydrophobic interactions, etc.) complexes and the initiation of intermolecular reactions. These reagents are particularly useful in directing peptide chemistry in the gas phase. Modified crown ethers, and 18-crown-6 ether (18C6) in particular, are used to bind specifically to various protonated primary amines, including the protonated side chain of lysine. The methods of the invention provide for an efficient method to enhance the binding energy, which is a critical factor influencing the success of these crown ether reagents. The binding energy must exceed any reaction barriers to the desired chemistry, otherwise simple dissociation of the complex occurs.

Due to the reagents ability to recognize specific amino acid residues, they also find utility in diagnostic applications, for example the reagents can be linked to a detectable label by methods that are well known in the art, and be used as probes to detect amino acid residues or sequences of interest.

The Reagents

The reagents of the invention are compounds capable of selectively forming non-covalent complexes and initiating intermolecular reactions with amine-containing compounds, particularly in the gas phase. In one embodiment, these reagents comprise at least one crown ether group and a moiety selected from acidic groups, transition metal binding groups and diazo groups. The groups are typically attached to the crown ether by an ether or ester linkage.

Crown Ethers

The crown ethers useful in the invention include those cyclic ethers having four or more oxygen atoms. Suitable crown ethers include, by way of illustration and not limitation, 18-crown-6 ether, 12-crown-4 ether. The reagent can have one or more crown ether groups, with two crown ether groups being particularly preferred.

18-Crown-6 ether (18C6) is of particular interest because it is both synthetically flexible and amenable to non-covalent complexation. It is well known for its ability to bind both metal cations and protonated primary amines in both solution and in the gas phase (Bradshaw et al. in: G. W. Gokel (Ed.), Comprehensive Supramolecular Chemistry, vol. 1, Pergamon/Elsevier, Oxford, 1996, p. 35; and Maleknia et al. (1993) J. Am. Chem. Soc. 115:2837). This ability is particularly useful for the recognition of amino acids such as lysine, because the side chain of this amino acid terminates in a primary amine. 18C6 complexes protonated primary amines through a combination of three hydrogen bonds and ion-dipole interactions. Non-covalent complexes with 18C6 bound to protonated primary amines can be transferred into the gas phase by electrospray ionization mass spectrometry (ESI-MS). When added to a solution containing a peptide, the 18C6 complex with the peptide is typically the most abundant peak in the spectrum (Julian et al. (2001) Int. J. Mass. Spectrom. 210:613). Appropriately modified lariat crown ethers behave similarly, forming non-covalent complexes that can be transferred to the gas phase as shown previously (Julian et al. (2002) J. Am. Soc. Mass Spectrom. 13:493).

Acidic Groups

Reagents containing an acidic group are particularly suited for the selective cleavage of peptide bonds. Suitable acidic groups include, by way of illustration and not limitation, benzoic acid and sulfonic acid.

An exemplary reagent having an acidic group is:

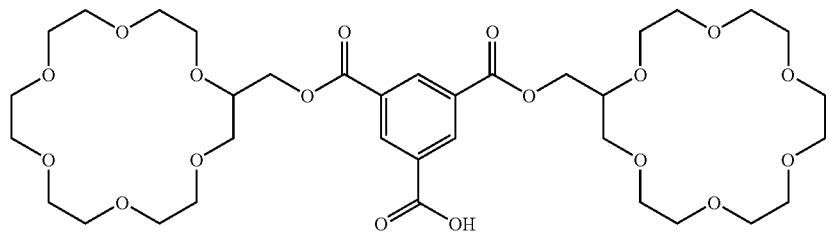

Transition Metal Binding Groups

Reagents containing a transition metal binding group, are particularly suited for the selective cleavage of peptide bonds. Suitable binding groups are well known in the art and include, by way of example and not limitation, alkyls, heteroalkyls, alkenyls, heteroalkenyls, aryls, heteroaryls, alkaryls, and alkheteroaryls.

Particularly suitable transition metal binding groups include, by way of illustration and not limitation, those groups noted above that contain from 2-6 amine groups and from 2-30 carbon atoms, commonly referred to as polyamines. Exemplary polyamines include, by way of illustration and not limitation, ethylenediamine, propylenediamine, butanediamine, hexamethylenediamine, N,N-dimethylethylenediamine, diethylenetriamine, dipropylenetriamine, triethylenetetramine, tetramethylethylenediamine, N,N-dimethylpropylenediamine, N,N,N'-trimethylethylenediamine, N,N,N',N'-tetramethyl-1,3-propanediamine, hexamethylenetetramine, diazabicyclononane, sparteine, phenantroline, 2,2'-bipyridine and neocuproine, with phenanthroline being particularly preferred.

Transition metal groups include those in Group 7 (e.g., manganese such as Mn(II)), Group 8 (e.g., iron such as Fe(III), ruthenium, osmium), Group 9 (e.g., cobalt such as Co(II), rhodium, iridium), Group 10 (e.g., nickel such as Ni(II), palladium such as Pd(II), platinum), Group 11 (e.g., copper such as Cu (I) and Cu(II) and silver such as Ag(I)), and Group 12 (e.g., zinc such as Zn(I) and Zn(II)) of the Periodic Table of the Elements.

An exemplary reagent having a transition metal binding group is:

Diazo Groups

Reagents containing a diazo group ($=N_2$), are particularly suited to covalently attach to peptides utilizing carbene insertion chemistry. Combining the recognition and binding powers of crow ethers with an easily activated diazo group allows for the efficient generation of a highly reactive carbene within a non-covalent complex. Intermolecular insertion reactions initiated by the carbene can transform these non-covalent complexes into covalently bound molecules. These diazo-based reagents are highly versatile molecules capable of binding to, and with appropriate activation, becoming covalently attached to virtually any molecule that contains a primary amine.

The diazo group may be contained within any hydrocarbyl group, such as $C_{1-24}$ alkyl (preferably $C_{1-18}$ alkyl, more preferably $C_{1-12}$ alkyl, most preferably $C_{1-6}$ alkyl), $C_{2-24}$ alkenyl (preferably $C_{2-18}$ alkenyl, more preferably $C_{2-12}$ alkenyl, most preferably $C_{2-6}$ alkenyl), $C_{2-24}$ alkynyl (preferably $C_{2-18}$ alkynyl, more preferably $C_{2-12}$ alkynyl, most preferably $C_{2-6}$ alkynyl), $C_{5-20}$ aryl (preferably $C_{5-12}$ aryl), and $C_{5-20}$ aralkyl (preferably $C_{5-12}$ aralkyl). Suitable diazo groups include, by way of illustration and not limitation, —C($N_2$)—.

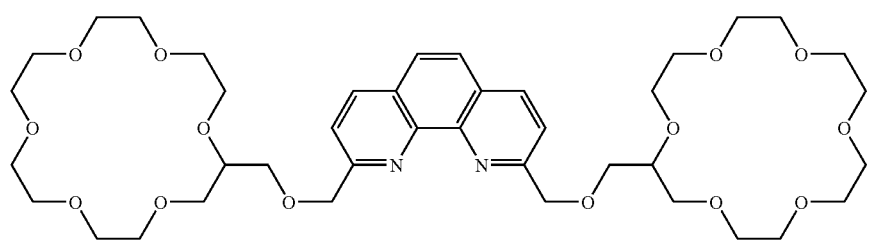

Exemplary reagents including diazo groups include, by way of example, and not limitation:

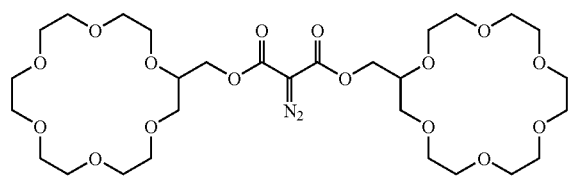

and

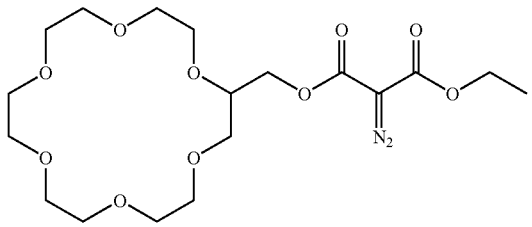

Method of Use

The compounds of the invention are capable of selectively forming non-covalent complexes and initiating intermolecular reactions with amine-containing compounds. In one embodiment, these reactions are conducted in the gas phase. However, it is also possible to effect similar chemistry in solution, with carbene formation initiated by either photochemical or metal catalyzed processes (Doyle et al. (1998) Modern Catalytic Methods for Organic Synthesis with Diazo Compounds, Wiley-Interscience, New York; Moody et al. (1992) Reactive Intermediates, Oxford University Press, New York, p. 26).

The amine-containing compound can contain at least one protonated amine. More particularly, the amine-containing compound can contain at least one primary amine. The reagents are particularly useful in peptide chemistry and therefore, in one embodiment of the invention, the amine-containing compound is an amino acid or a peptide. Exemplary amino acids include natural amino acids such as, by way of illustration and not limitation, arginine (R), glutamine (Q), asparagine (N), lysine (K), and hydroxylysine; as well as non-natural amino acids such as, by way of illustration and not limitation, α,δ-diaminovaleric acid (ornithine), α,γ-diaminobutyric acid, 2,3-diaminopropionic acid, and citrulline. Similarly, the peptide amine-containing compound will contain at least one amino acid selected from arginine, glutamine, asparagine, lysine, hydroxylysine, α,δ-diaminovaleric acid (ornithine), α,γ-diaminobutyric acid, 2,3-diaminopropionic acid, and citrulline. In one preferred embodiment, the peptide contains at least one lysine residue.

The compounds of the invention are particularly useful in methods of selectively forming non-covalent complexes and initiating intermolecular reactions with amine-containing compounds, comprising reacting the amine-containing compound with a compound of the invention, which comprises at least one crown ether group and a moiety selected from acidic groups, transition metal binding groups and diazo groups. With appropriate modifications, the compounds described herein can also serve as chemical cross-linkers, probes and sequence specific binding agents.

One embodiment of the invention is method of initiating peptide backbone cleavage at specific amino acid residues comprising adding a compound to the peptide, where the compound comprises at least one crown ether group and a moiety selected from acidic groups and transition metal binding groups. For example, the compounds of the invention are suitable for use in initiating selective cleavage of the peptide backbone, for example, near lysine residues.

Another embodiment of the invention is method of covalently attaching amino acids via carbene insertion chemistry comprising adding a compound to the amino acid, where the compound comprises at least one crown ether group and a diazo group. For example, the compounds of the invention are suitable for covalent attachment to peptides, for example lysine-containing peptides, following appropriate activation which generates a reactive carbene center.

The compounds of the invention can be used to recognize and bind to specific sequences in peptides and proteins. In particular, by binding to proteins, these compounds may be useful to modulate (inhibit or activate) protein functions, for example, the compound may bind to the protein and inhibiting protein folding, or inhibit protein activity by binding to an active site and block ligand binding.

Due to ability of the compounds of the invention to recognize specific amino acid residues, they also find utility in diagnostic applications. The compound can be linked (directly or indirectly through a linker) to a detectable label, i.e., any molecule which produces or can be induced to produce a signal, by methods that are well known in the art, and then be used as a probe to detect amino acid residues or sequences of interest by assay methods that are also well established in the art. Exemplary labels include radioactive moieties (e.g., $^{125}$I, $^{35}$S, $^{32}$P and $^{3}$H); fluorescent moieties (e.g., fluorescein, 6-carboxyfluorescein, isothiocyanate, Texas Red, rhodamine and rhodamine compounds such as tetramethylrhodamine, dansyl fluorophores, coumarins and coumarin derivatives, fluorescent acridinium moieties, benzopyrene based fluorophores, phycoerythrin, phycocyanin, allophycocyanin, o-phthaldehyde, and fluorescamine), chemiluminescent moieties (e.g., isoluminol), and bioluminescent moieties, as well as other luminescent moieties (e.g. luciferin and acridinium esters); phosphorescent moieties; colorimetric moieties; near IR-detectable moieties (e.g. dicyanines and La Jolla Blue dye); coupling agents (e.g., biotin, streptavidin, and avidin); magnetic and paramagnetic moieties; enzymes (e.g., alkaline phosphatase, glucose-6-phosphate dehydrogenase, and horseradish peroxidase); metal sol (e.g., gold sol) and so forth.

All patents, publications, and other published documents mentioned or referred to herein are incorporated by reference in their entireties.

It is to be understood that while the invention has been described in conjunction with the preferred specific embodiments thereof, that the foregoing description as well as the examples that follow, are intended to illustrate and not limit the scope of the invention. It should be understood by those skilled in the art that various changes may be made and equivalents may be substituted without departing from the scope of the invention, and further that other aspects, advantages and modifications will be apparent to those skilled in the art to which the invention pertains.

EXAMPLES

The practice of the present invention will employ, unless otherwise indicated, conventional techniques of synthetic organic chemistry, biochemistry, and the like, which are within the skill of the art. Such techniques are explained fully in the literature. See, for example, Oligonucleotide Synthesis (M. J. Gait, ed., 1984); *The Practice of Peptide Synthesis* (M.

Bodanszky and A. Bodanszky, 2$^{nd}$ ed., Springer-Verlag, New York, N.Y., 1994); Kirk-Othmer's *Encyclopedia of Chemical Technology*; and House's *Modern Synthetic Reactions*.

In the following examples, efforts have been made to insure accuracy with respect to numbers used (e.g., amounts, temperature, etc.) but some experimental error and deviation should be accounted for. Unless indicated otherwise, temperature is in degrees C. and pressure is at or near atmospheric. All solvents were purchased as HPLC grade, and all reactions were routinely conducted under an inert atmosphere of argon unless otherwise indicated. All reagents were obtained commercially unless otherwise indicated.

Background to Experimentals

Mass Spectrometry

All spectra were obtained using a Finnigan LCQ quadrupole ion trap mass spectrometer without modification. The critical instrument settings that yielded adduct formation include capillary voltage 5-15V, capillary temperature 200° C., and tube lens offset 30 to 50V. Higher capillary temperatures can dissociate the non-covalent complexes. The tube lens offset controlled the acceleration of ions as they left the capillary region. The tube lens voltage was minimized to avoid collisions with the He buffer gas. Soft sampling was important for the detection of the non-covalent complexes.

Sample concentrations were typically kept in the ~10 to 100 μM range for all species of interest. All samples were electrosprayed in a mixture of 80:20 methanol/water. The appropriate host was added to the sample and electrosprayed with the guest in order to observe adduct formation. Collision activated dissociation (CAD) was performed by isolating and then exciting the isolated peak by colliding it with He buffer gas. Samples were electrosprayed with a flow of 3-5 μL/min from a 500 μL Hamilton syringe for optimal signal. Silica tubing with an inner diameter of 0.005 in. was used as the electrospray tip.

Semi-empirical calculations were performed on HyperChem 5.1 Professional Suite using the PM3 parameter set. Calculations to determine the singlet/triplet splittings were performed on structures fully optimized at the B3LYP/CCPVTZ(-F)$^+$ level of theory. Comparison of this methodology with previous computational and experimental results for the following carbenes: $CH_2$, HCCl, HCF, $CCl_2$, $CF_2$, and HCCHO yielded results within (on average) ±0.6 kcalmol$^{-1}$ of the best experimental or theoretical value (Scott et al. (2001) *J. Am. Chem. Soc.* 123:6069-6076). Zero-point energy corrections were not included. Reactions were modeled at the B3LYP/6-31G** level of theory by minimizing structures containing both reactants, with several different starting geometries. Initial geometries included likely starting points for the most probable reaction mechanisms, that is, hydrogen abstraction, concerted insertion, and ylide formation. The DFT calculations were carried out using Jaguar 4.1 (SchrLdinger, Inc., Portland, Oreg.).

Calculations

The energetics of the carbene insertion reactions were quantitatively evaluated by carrying out reactions with the commercially available 2-diazo-malonic acid dimethyl ester:

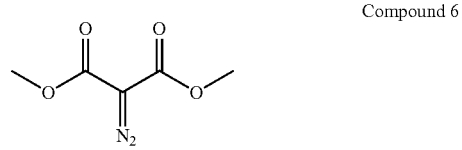

Compound 6

The structures of all reactants were fully minimized, and several different reaction mechanisms were tested. Initial structures included likely starting points for hydrogen abstraction, concerted insertion, and ylide formation. The starting structures for each of these possibilities corresponded respectively to: one hydrogen directed at the carbene, symmetrical presentation of the H—C—H or O—H bonds, and one lone pair directed at the carbene. The DFT calculations were carried out using Jaguar 4.1 (Schrödinger, Inc., Portland, Oreg.). PM5 semi-empirical calculations were carried out using CACHe Worksystem Pro 5.04 (Fujitsu, Inc., Beaverton, Oreg.).

Experimental Details for Syntheses

Due caution was used in the handling of diazo compounds. Reactions were performed in flame-dried glassware under a nitrogen atmosphere. Solvents were dried and purified using activated alumina columns. Diethylamine was distilled from $CaH_2$. 18-Crown-6-methanol was dried prior to use by heating (~100° C.) under vacuum. All other reagents were used as received from commercial sources. Reaction temperatures were controlled by an IKAmag temperature modulator.

Example 1

Compound Synthesis

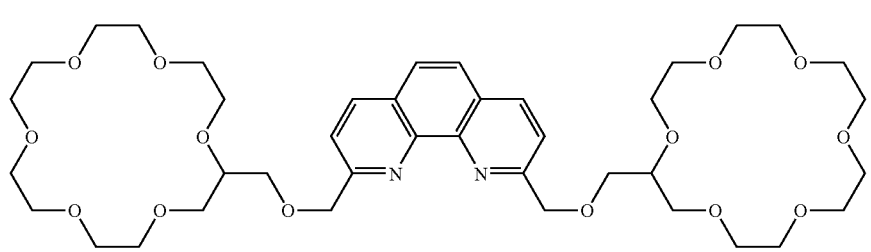

Synthesis of Compound 1

To a stirred solution of diethylamine (13 μL, 0.123 mmol) in THF (500 μL) at 0° C. was added nBuLi (60 μL, 2.1 M, 0.126 mmol) dropwise. The mixture was stirred for 10 min and then transferred via syringe to a solution of 18-crown-6-methanol (30 μL, 0.109 mmol) in THF (500 μL) stirred at 78° C. The solvent was removed under reduced pressure as the reaction warmed to room temperature. Excess diethylamine was removed by two consecutive additions of THF (1 mL) and removal under reduced pressure. The residue was then redissolved in THF (1 mL) and 2,9-bis(bromomethyl)-1,10-phenanthroline (Chandler et al. (1981) *J. Heterocycl. Chem.* 18:599; Weijnen et al. (1992) *J. Chem. Soc. Perkin Trans.* 2:830) (19 mg, 0.052 mmol) in CH$_2$Cl$_2$ (4 mL) was added. The resulting solution was stirred for 24 h, and then ether (10 mL) was added to precipitate the salt byproduct, which was removed by filtration through celite. The removal of solvent under reduced pressure yielded compound 1 (37.5 mg, 0.047 mmol, 91% yield) in sufficient purity for experimental use.

Synthesis of Compounds 2 and 3

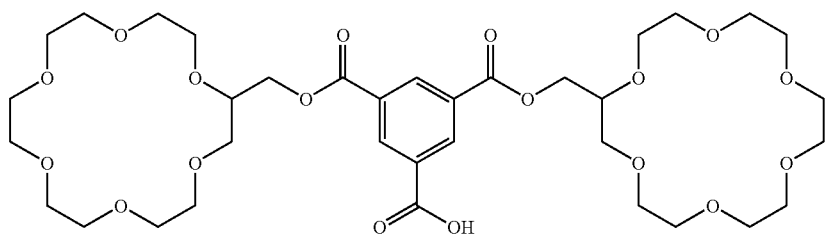

Compound 2, R is hydrogen
Compound 3, R is methyl

To a stirred solution of 18-crown-6-methanol (47 μL, 0.150 mmol), triethylamine (25 μL, 0.179 mmol), and dichloromethane (4.5 mL) was added 1,3,5-benzenetricarbonyl trichloride (20.4 mg, 0.077 mmol). The mixture was heated to reflux for 12 h, and then H$_2$O (1.5 mL) was added and the mixture was again heated to reflux for 1 h. The solvent was removed under reduced pressure, the residue dissolved in a minimal amount of dichloromethane (500 mL), and the undesired salts were precipitated out of solution with the addition of ether (5 mL). Filtration through celite and removal of solvent under reduced pressure yielded compound 2 (54.2 mg, 0.071 mmol, 95% yield) in sufficient purity for experimental use.

An identical procedure as that for the formation of compound 2 was followed with the exception that the reaction was quenched with MeOH (500 μL) instead of H$_2$O to yield compound 3 (49.1 mg, 0.063 mmol, 82% yield) in sufficient purity for experimental use.

Synthesis of Compounds 4 and 5

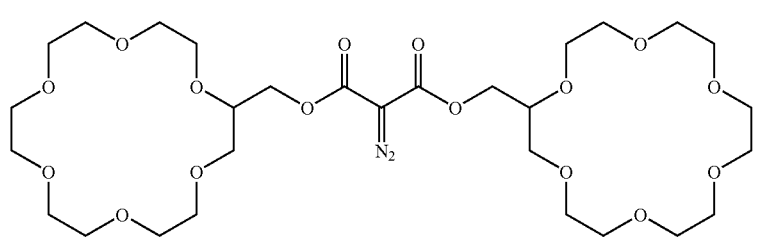

Compound 4

Compound 5

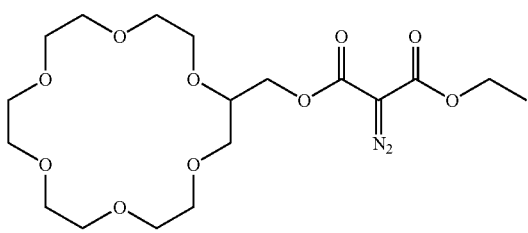

Compounds 4 and 5 were prepared according to established techniques (Julian et al. (2003) *Angew. Chem. Int. Ed.* 42:1012).

Example 2

Selective Cleavage of Peptide Bonds

Transition Metal Binding Functionality

Transition metals have been observed to influence peptide dissociation in previous gas phase experiments (Hu et al. (1995) *J. Am. Chem. Soc.* 117:11314; Nemirovskiy et al. (1998) *J. Am. Soc. Mass Spectrom.* 9:1285). Reagents were studied to determine usefulness of the reactivity of transition metals for the selective cleavage of peptide bonds. Compound 1 consists of two 18C6 ethers linked by a phenanthroline moiety, which can bind a variety of transition metals. ESI-MS of compound 1, copper (I), and KK indicated that compound 1 formed an abundant non-covalent complex with the peptide KK and copper (I). Collisional activation of the base peak $[1+KK+Cu+H]^{2+}$ resulted primarily in dissociation of the complex into $[1+Cu]^+$ and $[KK+H]^+$ with an additional prominent peak corresponding to the loss of 44 Da from $[KK+H]_+$. This loss is most likely explained as elimination of $CO_2$ from the C-terminus. In FIG. 1c, collisional activation of the much less abundant complex $[1+KK+Cu+2H]^{3+}$ yielded the loss of $CO_2$ directly. In the absence of the copper (I) ion, no loss of 44 Da was observed for either charge state, suggesting that copper (I) effectively initiates this reaction.

This chemistry was found to only occur with very short peptides that end with KK or RK, and compound 1 did not initiate any other cleavages. A wide variety of peptides and different transition metals including Ag(I), Fe(III), Co(II), Zn(I), Zn(II), Mn(II), Ni(II), Pd(II), and Cu(II) were tested. Many of these experiments failed to produce an abundant non-covalent complex, and when the complex was formed and isolated the result was simple dissociation in every case where the peptide contained an internal KK sequence.

These results can be rationalized by insufficient binding energy of the non-covalent complex in the gas phase. The presence of a cationic transition metal trapped between two positively charged lysine residues results in unfavorable coulombic interactions that effectively reduce the binding energy of the complex. The binding energy was reduced by ~80±10 kcal/mol by inserting a singly charged transition metal ion as determined by PM5 calculations. This explains why only minimal complexation (or none) occurs for internal KK sequences, and the reduced binding also leads to the exclusive dissociation of these complexes upon collisional activation. A deprotonated C-terminus effectively mitigates the unfavorable interactions and increases the binding energy by neutralizing the central positive charge. Therefore, compound 1 was determined to be particularly suitable for selectively attaching near the C-terminus of peptides that end in KK or RK/KR; however it was less effective at cleaving peptides in the gas phase.

Acidic Functionality

As mentioned before, selective cleavage at aspartic acid residues has been observed in the gas phase previously, indicating that acid/base chemistry may provide an alternate route for cleaving peptides in the gas phase (Tsaprailis et al (2000) *Int. J. Mass Spectrom.* 195/196:467; Tsaprailis et al. (1999) *J. Am. Chem. Soc.* 121:5142; Lee et al. (1998) *J. Am. Chem. Soc.* 120:3188). Compound 2 was designed based upon this premise. Compound 2 contains two 18C6 ethers linked by benzoic acid. Deprotonation of the acid is assisted by favorable electrostatic interactions upon complexation with two protonated lysine residues. The ESI mass spectrum for a solution of compound 2 and KKKK (SEQ ID NO: 8) demonstrated excellent recognition. The doubly charged adduct $[2+KKKK+2H]^{2+}$ formed the base peak in the spectrum. Collisional activation of this peak resulted primarily in dissociation of the complex. However, there were additionally two peaks corresponding to the loss of water and the N-terminal lysine. To verify that this chemistry was initiated by the benzoic acid, an additional experiment was conducted where the acid was converted to a methyl ester (compound 3). The results were nearly identical as for compound 2, suggesting that compound 2 is merely a spectator adduct, which was sufficiently strongly bound to remain attached after a covalent bond cleavage has occurred but did not directly affect the cleavage process, i.e., did not initiate the cleavage of the N-terminal lysine.

Earlier studies of selective cleavages at aspartic acid residues suggest that this process is favored due to the proximity of the aspartic acid side chain to the peptide backbone, with acidity enhanced by a proximal positive charge (Tsaprailis et al (2000) *Int. J. Mass Spectrom.* 195/196:467; Tsaprailis et al. (1999) *J. Am. Chem. Soc.* 121:5142). The observation that the similar reactivity of glutamic acid (with the addition of a single methylene) is greatly reduced in comparison suggests that the reaction has very special geometrical constraints. It may be that the acidic group in compound 2 cannot exploit the same reaction pathway as inferred for aspartic acid cleavages because it is not held in close proximity to the peptide backbone. Nevertheless, the results from compound 2 are important because they demonstrate that biomimetic reagents with multiple crown ethers have sufficient binding energy to mitigate dissociation in favor of peptide cleavage processes.

Example 3

Reaction with 1,6-Diaminohexane

In this example, intermolecular reactions were successfully initiated in noncovalent clusters. First, a strongly bound host-guest complex was formed in solution and transferred to the gas phase by ESI. Second, a diazo group that was incorporated into the host was efficiently and easily converted into a highly reactive carbene (A neutral, two-electron carbene was formed. Other studies have focused on carbene radical cations such as $[CH^2]^+$, see for example, Flammang et al. (2002) *Int. J. Mass Spectrom.* 202:A8-A25) by low-energy collision-activated dissociation (CAD) (Marzluff et al., in Large Ions: Their Vaporization, Detection, and Structural Analysis, eds. Baer et al., Wiley, New York, 1996, pp. 115-143; McLuckey (1992) *J. Am. Soc. Mass Spectrom.* 3:599-

614; and Hayes et al. (1990) *Methods Enzymol.* 193:237-263). This carbene then reacted in an intermolecular fashion, covalently binding the host-guest complex (Rice et al. (1934) *J. Am. Chem. Soc.* 56:2381-2383; Herzberg (1961) *Proc. R. Soc. London Ser. A* 262:291-317; Carbenes, Vols. 1 and 2, eds.: Moss et al., Wiley, New York, 1973, 1975; Rynbrandt et al. (1970) *J. Phys. Chem.* 74:4175-4176; Rynbrandt et al. (1971) *J. Chem. Phys.* 54:2275-2276; Poutsma et al. (1997) *J. Am. Chem. Soc.* 119:4686-4697; Paulino et al. (1991) *J. Am. Chem. Soc.* 113:5573-5580; Leopold et al. (1985) *J. Chem. Phys.* 83:4849-4865, and references noted therein; Bertani et al. (1997) *Organometallics* 16:3229-3233; Doyle et al., Modern Catalytic Methods for Organic Synthesis with Diazo Compounds, Wiley-Interscience, New York, 1998; Moody et al. Reactive Intermediates, Oxford University Press, New York, 1992, pp. 26-50).

Compound 4 was designed to bind molecules with either one or, preferentially, two protonated primary amines, while compound 5, with a single 18C6 unit, binds to a single protonated primary amine. Compound 6 was used as a model compound in computations.

The complex between compound 6 and doubly protonated 1,6-diaminohexane (DAH) forms in solution, and was transferred intact to the gas phase by ESI. The complex was isolated and subjected to CAD. The sole product resulted from a neutral loss of 28 Da, which was interpreted to be the loss of $N_2$ from the diazo group. Significantly, the data observed provided evidence for covalent-bond cleavage in preference to dissociation of the complex. The loss of $N_2$ from the diazo group should yield the corresponding carbene (:6) as a highly reactive, short-lived intermediate. This carbene can then undergo either intermolecular or intramolecular reaction.

The complex product was subjected to further collisional activation. The majority of the product-ion intensity resulted from covalent-bond cleavage with loss of a crown, or part of a crown and retention of DAH. The fragmentation of the host without the accompanying loss of the guest provided evidence that an intermolecular reaction involving covalent coupling between the host and guest occurred by C—H insertion of the carbene. For the doubly protonated DAH, the complexation of the protonated primary amines by the crown ethers reduced the likelihood of an N—H insertion reaction by the carbene (18C6 locks protons onto primary amines; see Julian et al. (2001) *Int. J. Mass Spectrom.* 210:613-623 and Lee et al. (1998) *J. Am. Chem. Soc.* 120:5800-5805). It was also observed that some of the DAH appeared to dissociate from the complex, which suggested that an intramolecular process was competitive in this case. (A Wolff rearrangement is a likely competing reaction for the carbene; see, for example Likhotvorik et al. (2001) *J. Am. Chem. Soc.* 123:6061-6068 and Scott et al. (2001) *J. Am. Chem. Soc.* 123:6069-6076).

Singly charged DAH had a lower binding energy to compound 1 than the doubly charged species, yet it was found that [:4+DAH+H]$^+$ was generated with high efficiency from the [1+DAH+H]$^+$ complex. The loss of nitrogen was accompanied by an additional loss of 294 Da, which was accounted for by the loss of 18-crown-6 methanol. This additional loss was observed for all complexes of both compounds 4 and 5 in which there was an unprotonated primary amine or alcohol available (in experiments with compound 5, the loss of ethanol was also observed). DFT calculations at the B3LYP/CCPVTZ(-F)$^+$ level on compound :6 described a singlet ground state, with a singlet/triplet splitting of 3±1 kcalmol$^{-1}$. This result suggested that the singlet state was certainly accessible and perhaps favorable, which is in agreement with experimental results. Both results obtained in the work described herein and in Richardson et al. (1971) *J. Am. Chem. Soc.* 93:3790-3791, where Wolff rearrangement is observed, must proceed through the singlet state. DFT calculations at the B3LYP/6-31G** level on :6 and methylamine led to the formation of an ammonium ylide without a barrier. The ammonium ylide was a local minimum on the potential energy surface, and previous reports have suggested that all carbenes will initially react with amines by the formation of an intermediate ylide (Pliego et al. (1999) *J. Phys. Chem. A* 103:3904-3909). From this ammonium ylide two reaction pathways with minimal barriers were possible, as shown below:

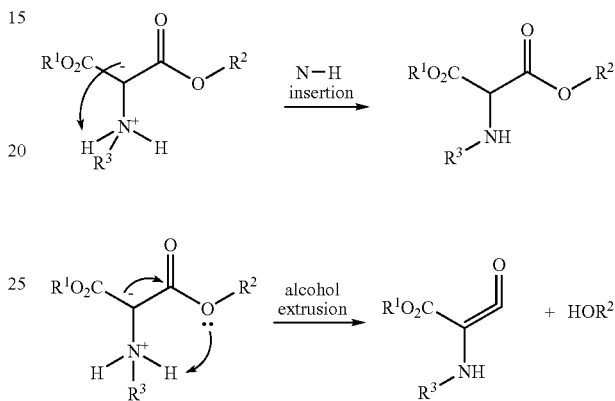

Both pathways lead to covalent attachment of the host-guest complex through intermolecular reactions; one route leads to formal N—H insertion, and the other leads to the loss of an alcohol group and the generation of a ketene.

Further excitation of the isolated [:4+DAH+H]$^+$ species, after the loss of nitrogen, led exclusively to the loss of 294 Da. The N—H insertion product shown in the pathways above, is protonated at the secondary amine. Transfer of this proton to the ester can lead to the 294 Da loss observed, by alcohol extrusion. It is also possible, though unlikely, that the ammonium ylide, could be sufficiently long-lived to yield this product directly.

MS/MS/MS analysis of [:4+DAH+H–294]$^+$ offered several critical results. First, a loss of 28 Da was probably a result of the loss of CO from the ketene product shown in the pathway above. Second, the fragment being subjected to further collisional activation contained only a single remaining crown. The primary losses were multiple (CH$_2$CH$_2$O) fragments from this remaining crown. The data revealed the sequential removal of almost the entire remaining crown ether without the loss of the guest molecule. In the absence of both crowns, retention of the guest can only be explained by a newly formed covalent bond.

These studies demonstrate that reagents that bind to specific functional groups in complex molecules can be derivatized to introduce the means to covalently couple them to target molecules with appropriate methods of activation. 18C6, which binds strongly to protonated primary amines (Julian et al. (2001) *Int. J. Mass Spectrom.* 210:613-623, was combined with a diazo precursor to a reactive carbene to form a potent reagent that can be used to target lysines in peptides or proteins.

Example 4

Selective Cleavage of Peptide Bonds

Although the cleaving of peptide bonds remains an important goal, covalent attachment to peptides is another important reaction that is often used for cross-linking peptides and proteins (Steen et al. (2002) *Mass Spectrom. Rev.* 21:163). Compounds 4 and 5 ("molecular mousetraps") were designed to covalently attach to peptides containing lysine residues or any other molecule which contains a protonated primary amine. Both compounds 4 and 5 contain a reactive diazo group, which yields a highly reactive carbene upon collisional activation. Experimental and theoretical results for the interactions of compound 4 with 1,6-diaminohexane have been reported previously (Julian et al. (2003) *Angew. Chem. Int. Ed.* 42:1012). In order to understand the underlying chemistry, several experiments were performed with simple small molecules to further elucidate the reaction pathways.

Reactions with Small Molecules

The ESI-MS spectrum for a solution of 1-aminohexane ($H_2N(CH_2)_5CH_3$; compound A) and compound 4 demonstrated excellent recognition. The complex corresponding to [4+A+H]$^+$ clearly formed the base peak in the spectrum, demonstrating the excellent recognition of compound 4 for protonated primary amines. This complex was subjected to collisional activation. The loss of $N_2$ was the only major product observed, yielding the reactive carbene (denoted by :4) in nearly 100% yield. Theoretical results at the B3LYP/6-31G** level with methane and the similar carbene :6 suggest that C—H insertion occurred with little or no barrier in a concerted fashion (Note that the insertion reaction only occurred when the H—C—H bond was presented symmetrically to the carbene, suggesting a minimal barrier may exist. Higher level DFT calculations at the at the B3LYP/CCPVTZ (-F)+ level on :6 yield a singlet ground state with a singlet/triplet splitting of 3±1 kcal/mol suggesting that these reactions may proceed through the singlet state). The carbene (:4) was also shown to react with compound A by C—H insertion at various points along the hydrocarbon chain. This was confirmed when no dissociation of compound A was observed after further collisional activation. Instead several covalent bond cleavages were observed, corresponding to the loss of a $CH_2CH_2O$ link from 18C6 and another corresponding to the loss of an entire crown. This suggests that C—H insertion did in fact occur and led to the covalent attachment of the host/guest complex.

Hydroxyl groups are found in three amino acid side chains and can exhibit enhanced reactivity towards carbenes. CAD experiments were conducted with compound 4 and 1,6-aminohexanol ($H_2N(CH_2)_6OH$; compound B) which was used as a model compound. The MS$^2$ spectrum for the CAD of [4+B+H]+led to similar results to those obtained previously for 1,6-diaminohexane (Julian et al. (2003) *Angew. Chem. Int. Ed.* 42:1012). The initial loss of $N_2$ was accompanied by an additional loss of 18C6-$CH_2OH$. The MS$^3$ spectrum for the CAD of [: 4+B+H]$^+$ indicated that the loss of $CH_2CH_2O$ led to a base peak, while the loss of 18C6-$CH_2OH$ was secondary. The loss of $CH_2CH_2O$ was not present in the MS$^2$ spectrum. This suggests that the loss of 18C6-$CH_2OH$ in the MS$^2$ spectrum and MS$^3$ spectrum proceeded by two different reaction mechanisms and that the two products produced are generated competitively rather than consecutively.

The two proposed reaction pathways are shown below and are similar to those proposed for the comparable 1,6-diaminohexane system (Julian et al. (2003) *Angew. Chem. Int. Ed.* 42:1012, and described in Example 3).

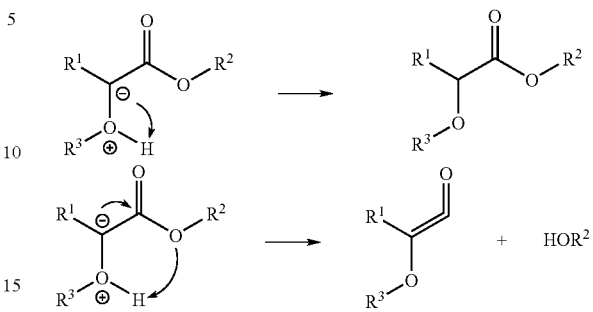

DFT calculations on :6 and $H_2O$ at the B3LYP/6-31G** level support the formation of an intermediate oxonium ylide. The formation of the ylide proceeded without barrier from several different starting geometries. Precedence for this mechanism can be found in previous studies, which have revealed oxonium ylide formation in reactions of various alcohols with carboethoxycarbene, a closely related molecule (Toscano et al. (1994) *J. Am. Chem. Soc.* 116:8146). All of the experimental and theoretical data support the reaction mechanisms shown above for any system with an alcohol (unprotonated amines react by a very similar pathway as shown previously) (Julian et al. (2003) *Angew. Chem. Int. Ed.* 42:1012). In fact, the additional loss of 294 in the MS$^2$ spectrum is indicative of the presence of alcohols and amines. Further excitation of the complex following the loss of one 18C6 was shown to result primarily in the loss of the other 18C6 without the accompanying loss of any of compound B. In the absence of both crowns, the retention of compound B can only be explained by an insertion reaction which has transformed the non-covalent complex into a molecule.

Compound 5 contains only a single crown ether connected to a diazo functional group, with an ethyl ester connected to the side opposite 18C6. Allylamine ($H_2NCH_2CHCH$; compound C) and 1,4-diaminobutane ($H_2N(CH_2)_4NH_2$; compound D) were complexed with compound 5. Collisional activation of the complex [5+C+H]$^+$ resulted primarily in the loss of $N_2$. Further excitation of the product peak yielded the loss of neutral EtOH and a multitude of other peaks. However, dissociation of compound C was not observed, suggesting that covalent attachment had been achieved. Carbene insertion into double bonds is a well documented phenomena in solution and is the most likely explanation for the results observed here (Moss et al. (Eds.), Carbenes, vols. 1 and 2, Wiley, New York, 1973, 1975).

Experiments with compound D and compound 5 yielded results similar to those obtained with compound 4 and protonated 1,6-diaminohexane except that the loss of EtOH was observed in addition to the loss of 18C6-$CH_2OH$. The MS$^2$ spectrum revealed that the loss of EtOH was approximately twice as abundant as the loss of 18C6-$CH_2OH$. This is consistent with the proposed reaction mechanisms. A fragment that contains no 18C6 was subjected to CAD, and Compound D (mass 88 Da) did not dissociate from the complex. Since there was no crown ether present to bind to a primary amine, this data offers compelling evidence that indeed what was once a non-covalent complex is now a molecule.

All of the data obtained by reactions with small molecules suggests that covalent attachment occurs rapidly and almost exclusively when the complex containing compound 4 or compound 5 was subjected to CAD. The corresponding carbenes (:4 and :5) can undergo insertion reactions with a wide variety of different functional groups.

Reactions with Peptides

After ascertaining that the compounds of the invention can complex with small molecules, the compounds were studied to ascertain whether they would covalently attach to peptides.

Compound 4 was designed to bind to peptides containing two lysine residues. The ESI spectrum for compound 4 complexed with the simple peptide KGK (SEQ ID NO:1) indicated abundant adduct peaks are observed, demonstrating excellent recognition. The $[4+KGK+2H]^{2+}$ peak was subjected to collisional activation. The loss of $N_2$ lead to the base peak in the spectrum, with an additional loss of 294 Da being observed as well. No dissociation was observed, suggesting that the appropriate combination of high binding energy and low activation barriers was achieved for compound 4. Further collisional activation did not lead to any dissociation of KGK (SEQ ID NO:1), again confirming that an intermolecular reaction had occurred. Very similar results were obtained for other peptides containing two lysines in close proximity, such as INLKAIAALVKKVL (SEQ ID NO:2), AAKRKAA (SEQ ID NO:3), and KK (SEQ ID NO:4). When the singly charged $[4+KGK+H]^+$ complex was subjected to CAD, then a neutral loss of compound 4 yielded the only observed product. This appears to suggest that two crown ethers are necessary to achieve sufficient binding energy for the intermolecular reaction to occur. However, further experiments indicated that this is not the case.

Compound 5 only contains a single 18C6, and will therefore only bind to a single lysine, reducing the overall binding energy relative to compound 4. The MS spectrum showed that compound 5 formed abundant non-covalent complexes with KGK (SEQ ID NO:1). Isolation and collisional activation of the doubly charged complex $[5+KGK+2H]^{2+}$ resulted exclusively in the loss of $N_2$, generating a reactive carbene. Reisolation and further activation of this peak yielded fragments corresponding to the loss of the C-terminal and N-terminal lysine residues and the loss of 17 Da (presumably $NH_3$). Simple dissociation was not observed, indicating covalent attachment through an intermolecular reaction occurred. The loss of lysine from both termini of the peptide suggests that either attachment of the crown is not selective for one lysine over another, or that the insertion reaction is not selective, or both.

CAD of the singly charged $[5+KGK+H]^+$ complex again resulted in loss of the neutral compound 5 exclusively. The exact cause for this interesting behavior is not known, but the results can be explained by at least two possibilities. Either the binding energy of the complex was enhanced by the addition of a second proton, or the absence of the second proton enabled a lower energy dissociation pathway. Regardless of the cause, it was observed in general that complexes with higher charge states tended to favor intermolecular reactions, while lower charge state complexes tend to favor simple dissociation. In very similar reactions to those described above, compound 5 was covalently attached to many peptides including:

| | |
|---|---|
| INLKAIAALVKKVL, | (SEQ ID NO:2) |
| AAKRKAA, | (SEQ ID NO:3) |
| KPPGFSPFR, | (SEQ ID NO:5) |
| GGK, and | (SEQ ID NO:6) |
| GGKAA. | (SEQ ID NO:7) |

We claim:

1. A method of selectively forming non-covalent complexes and initiating intermolecular reactions with amine group-containing compounds, comprising reacting the amine group-containing compound with a second compound comprising: (1) at least one crown ether group containing four or more oxygen atoms; and (2) a moiety selected from acidic groups, transition metal binding groups and diazo groups, wherein the acidic group is a benzoic acid group, and wherein the transition metal binding group is a polyamine selected from ethylenediamine, propylenediamine, butanediamine, hexamethylenediamine, N,N-dimethylethylenediamine, diethylenetriamine, dipropylenetriamine, triethylenetetramine, tetramethylethylenediamine, N,N-dimethylpropylenediamine, N,N,N'-trimethylethylenediamine, N,N,N',N'-tetramethyl-1,3-propanediamine, hexamethylenetetramine, diazabicyclononane, sparteine, phenantroline, 2,2'-bipyridine and neocuproine and further wherein the amine-group containing compound is an amino acid, a peptide, or a protein.

2. The method of claim 1, wherein the crown ether is 18-crown-6 ether.

3. The method of claim 1, wherein the transition metal is selected from Ag(I), Fe(III), Co(II), Zn(I), Zn(II), Mn(II), Ni(II), Pd(II), Cu (I) and Cu(II).

4. The method of claim 1, wherein the diazo group is —C(N$_2$)—.

5. The method of claim 1, wherein the moiety is attached to the crown ether group through an ether or an ester linker.

6. The method of claim 1, wherein the amine group-containing compound comprises at least one protonated amine.

7. The method of claim 1, wherein the amine group-containing compound comprises at least one primary amine.

8. The method of claim 1, wherein the amine group-containing compound is a peptide or protein comprising at least one lysine.

9. The method of claim 1, wherein the formation of non-covalent complexes and initiation of intermolecular reactions is conducted in the gas phase.

10. The method of claim 1, wherein the formation of non-covalent complexes and initiation of intermolecular reactions is conducted in solution.

11. The method of claim 1, wherein the intermolecular reaction is the selective cleavage of a peptide backbone.

12. The method of claim 11, wherein the moiety is selected from acidic groups and transition metal binding groups.

13. The method of claim 1, wherein the non-covalent complex is formed with a peptide via carbene insertion chemistry.

14. The method of claim 13, wherein the moiety is a diazo group.

15. The method of claim 1, wherein the second compound further comprises a detectable label.

16. A compound capable of selectively forming non-covalent complexes and initiating intermolecular reactions with amine group-containing compounds, wherein the compound comprises: (1) at least one crown ether group containing four or more oxygen atoms; and (2) a moiety selected from acidic groups, transition metal binding groups and diazo groups, wherein the acidic group is a benzoic acid group, and wherein the transition metal binding group is selected from ethylenediamine, propylenediamine, butanediamine, hexamethylenediamine, N,N-dimethylethylenediamine, diethylenetriamine, dipropylenetriamine, triethylenetetramine, tetramethylethylenediamine, N,N-dimethylpropylenediamine, N,N,N'-trimethylethylenediamine, N,N,N',N'-tetramethyl-1,3-propanediamine, hexamethylenetetramine, diazabicyclononane, sparteine, phenantroline, 2,2'-bipyridine and neocuproine, and further wherein the amine-group containing compound is an amino acid, a peptide, or a protein.

17. The compound of claim 16, wherein the crown ether is 18-crown-6 ether.

18. The compound of claim 16, which comprises one crown ether group.

19. The compound of claim 16, which comprises two crown ether groups.

20. The compound of claim 16, wherein the moiety is an acidic group.

21. The compound of claim 16, wherein the moiety is a transition metal binding group.

22. The compound of claim 21, wherein the transition metal binding group is phenanthroline.

23. The compound of claim 21, wherein the transition metal is selected from Ag(I), Fe(III), Co(II), Zn(I), Zn(II), Mn(II), Ni(II), Pd(II), Cu (I) and Cu(II).

24. The compound of claim 16, wherein the moiety is a diazo group.

25. The compound of claim 24, wherein the diazo group is —C(N$_2$)—.

26. The compound of claim 16, wherein the moiety is attached to the crown ether group through an ether or an ester linker.

27. The compound of claim 16, which further comprises a detectable label.

* * * * *

SEQUENCE LISTING

<160> NUMBER OF SEQ ID NOS: 8

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 1

Lys Gly Lys
 1

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 2

Ile Asn Leu Lys Ala Ile Ala Ala Leu Val Lys Lys Val Leu
 1               5                  10

```
<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 3

Ala Ala Lys Arg Lys Ala Ala
  1               5

<210> SEQ ID NO 4
<211> LENGTH: 2
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 4

Lys Lys
  1

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 5

Lys Pro Pro Gly Phe Ser Pro Phe Arg
  1               5

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 6

Gly Gly Lys
  1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 7

Gly Gly Lys Ala Ala
  1               5

<210> SEQ ID NO 8
<211> LENGTH: 4
<212> TYPE: PRT
<213> ORGANISM: Artificial Sequence
<220> FEATURE:
```

```
<223> OTHER INFORMATION: Description of Artificial Sequence:
      Illustrative peptide

<400> SEQUENCE: 8

Lys Lys Lys Lys
 1
```